US011517527B2

(12) United States Patent
Smith et al.

(10) Patent No.: US 11,517,527 B2
(45) Date of Patent: Dec. 6, 2022

(54) SYSTEMS, DEVICES AND METHODS FOR MAKING AND EXPRESSING FOAM USED IN MEDICAL PROCEDURES

(71) Applicant: Ethicon, Inc., Somerville, NJ (US)

(72) Inventors: Nicole Smith, Hoboken, NJ (US); Michael Cardinale, Morristown, NJ (US)

(73) Assignee: Ethicon, Inc., Raritan, NJ (US)

( * ) Notice: Subject to any disclaimer, the term of this patent is extended or adjusted under 35 U.S.C. 154(b) by 1048 days.

(21) Appl. No.: 16/180,482

(22) Filed: Nov. 5, 2018

(65) Prior Publication Data
US 2020/0138713 A1  May 7, 2020

(51) Int. Cl.
| | | |
|---|---|---|
| *A61K 9/00* | (2006.01) | |
| *A61K 9/12* | (2006.01) | |
| *A61L 24/00* | (2006.01) | |
| *A61B 17/00* | (2006.01) | |
| *B01F 23/235* | (2022.01) | |

(Continued)

(52) U.S. Cl.
CPC ........ *A61K 9/122* (2013.01); *A61B 17/00491* (2013.01); *A61L 24/0036* (2013.01); *B01F 23/235* (2022.01); *B01F 25/4512* (2022.01); *B01F 33/50112* (2022.01); *B01F 35/7174* (2022.01); *A61B 17/12013* (2013.01); *A61B 2017/00495* (2013.01); *A61J 1/2048* (2015.05); *A61J 1/2096* (2013.01)

(58) Field of Classification Search
CPC ............ B01F 35/7174; B01F 33/50112; B01F 25/4512; B01F 23/235; A61K 9/122; A61J 1/2096; A61B 17/00491; A61L 24/0036

See application file for complete search history.

(56) References Cited

U.S. PATENT DOCUMENTS

| | | |
|---|---|---|
| 4,107,075 A | 8/1978 | Kramer |
| 5,480,597 A | 1/1996 | Ishida et al. |

(Continued)

FOREIGN PATENT DOCUMENTS

WO     2018020436     2/2018

OTHER PUBLICATIONS

WO2000072821A1 to Osman Published Dec. 7, 2000 (Year: 2000).*

(Continued)

*Primary Examiner* — Anshu Bhatia
(74) *Attorney, Agent, or Firm* — David R. Crichton

(57) ABSTRACT

A medical device for making foam includes a syringe having a plunger for dispensing a liquid from a liquid dispensing port, and a mixing chamber including a mixing chamber inlet, a mixing chamber outlet, a liquid flow channel extending between the mixing chamber inlet and the mixing chamber outlet, and a gas inlet channel that intersects with the liquid flow channel. The system has a gas cartridge containing the gas, a first gas conduit connected with the syringe, and a second gas conduit connected with the gas inlet channel. An actuator is coupled with the gas cartridge for releasing the gas into the first and second gas conduits. The released gas in the first gas conduit forces the plunger toward the liquid dispensing port for dispensing the liquid from the liquid dispensing port and into the liquid flow channel while the released gas in the second gas conduit flows into the gas inlet channel of the mixing chamber for mixing with the liquid in the liquid flow channel.

22 Claims, 10 Drawing Sheets

(51) Int. Cl.
  *B01F 25/451* (2022.01)
  *B01F 33/501* (2022.01)
  *B01F 35/71* (2022.01)
  *A61J 1/20* (2006.01)
  *A61B 17/12* (2006.01)

(56) References Cited

U.S. PATENT DOCUMENTS

| | | | |
|---|---|---|---|
| 6,276,459 B1 * | 8/2001 | Herrick | A62C 5/02 |
| | | | 169/14 |
| 7,537,174 B2 | 5/2009 | Redl et al. | |
| 8,449,494 B2 | 5/2013 | Melsheimer | |
| 9,155,874 B2 | 10/2015 | Mayazaki et al. | |
| 9,179,898 B2 | 11/2015 | Redl et al. | |
| 9,278,181 B2 | 3/2016 | Meron et al. | |
| 9,579,449 B2 | 2/2017 | Sharma et al. | |
| 2002/0077589 A1 | 6/2002 | Tessari | |
| 2015/0273154 A1 | 10/2015 | Piotrovski | |

OTHER PUBLICATIONS

International Search Report issued in corresponding International Application No. PCT/IB2019/059241, dated Jan. 13, 2020, 2 pages.
Plastic Materials: Porous Plastic PE, PP & PTFE Applications, www.porex.com/technologies/materials/porous-plastics/, Porex Corporation, 2 pages.

* cited by examiner

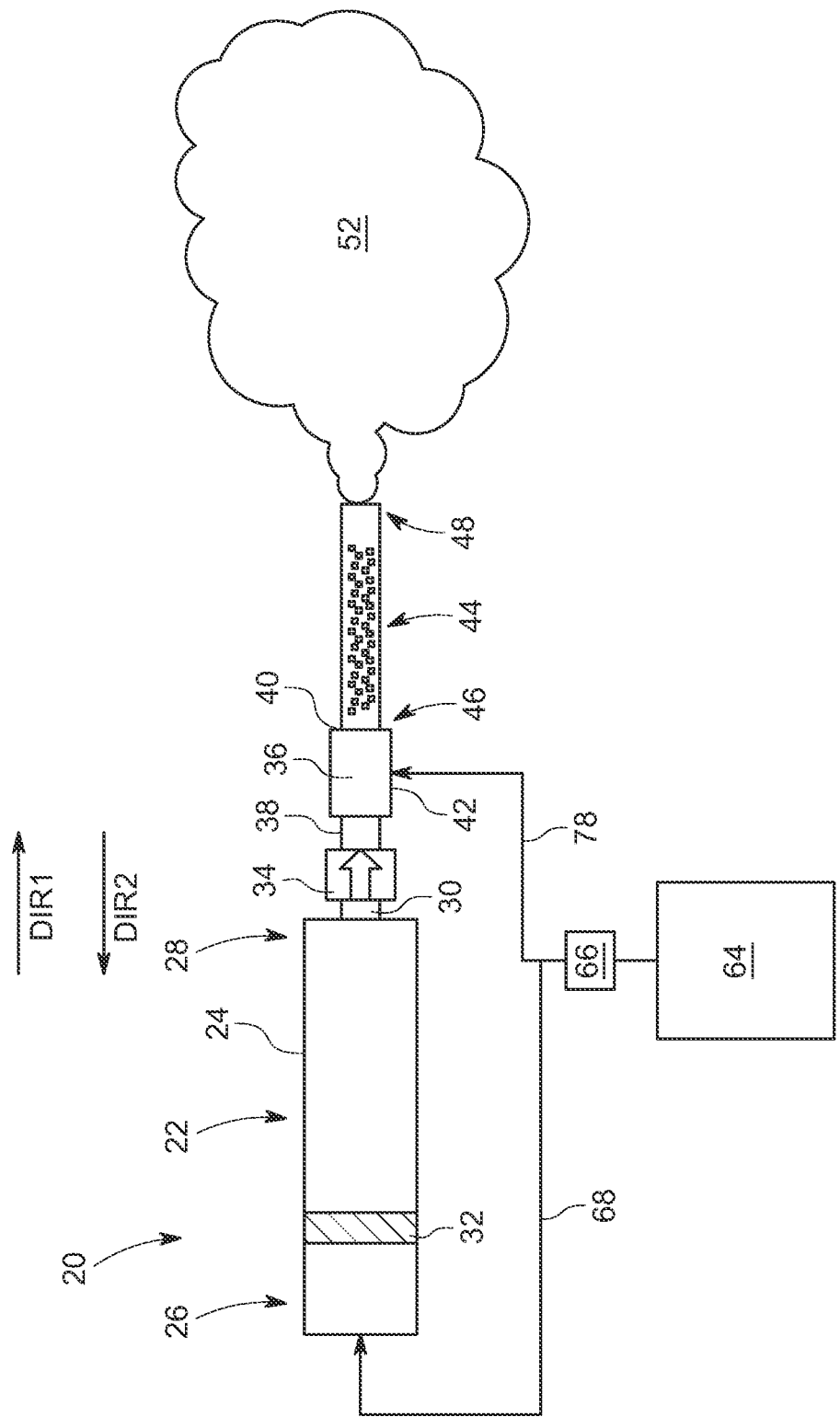

SYSTEMS, DEVICES AND METHODS FOR MAKING AND EXPRESSING FOAM USED IN MEDICAL PROCEDURES

BACKGROUND OF THE INVENTION

Field of the Invention

The present patent application is generally related to making foam on demand, and is more specifically related to systems, devices, and methods for making foam used in medical procedures for sealing leaks in tissue.

Description of the Related Art

Foam is formed by trapping pockets of gas in a liquid or solid. In most foams, the volume of gas is large, with thin films of liquid or solid separating the pockets of gas. In closed-cell foam, the gas forms discrete pockets, with each gas pocket being surrounded by solid material. In open-cell foam, the gas pockets connect to each other. A sponge is an example of an open-cell foam.

In the medical field, foam has a number of uses including applying foam to tissue to seal leaks (e.g., air leaks in lung tissue). When a foam sealant is used in medical procedures, in order to ensure the formation of a robust, efficacious seal, it is important for the foam to have uniformly spaced, micro-bubbles that are consistent in size and stable. The presence of any larger bubbles in the foam can act as a passageway for an air leak and compromise the seal created by the foam. If the foam is unstable and loses its shape, that may also compromise a seal.

Prior art foaming systems typically use canisters that are filled with both a liquid product and a liquid propellant. The liquid product often contains a surfactant, which facilitates making foam from the liquid product. When a valve on the canister is opened, the pressure on the liquid propellant is reduced, which causes the propellant to boil. Particles of the boiling propellant break free and form a pressurized gas layer at the top of the canister, which pushes the liquid product and the liquid propellant through a dip tube to an exit nozzle. Once the liquid product and the liquid propellant flows through the exit nozzle, the propellant expands into a gas that forms bubbles in the liquid product, which creates foam.

Using liquid propellants to make foam, however, causes a number of problems. For example, many liquid propellants are flammable, which creates a safety issue. As a result, flammable, liquid propellant systems are often banned from operating rooms. There are some non-flammable liquid propellant systems that are available on the market, however, there are numerous challenges associated with terminal sterilization of the propellants, which makes these systems risky to use during sterile, medical procedures.

Compressed gases, such a nitrogen, can also be used as the propellant for a canister containing a liquid product that foams. In this case, the liquid product often contains a surfactant, which facilitates making foam from the liquid product. When a valve on the canister is opened, the pressure of the gas pushes the liquid product through a dip tube to an exit nozzle. The dip tube has a vapor tap that allows compressed gas to perfuse into the flowing liquid product. Once the liquid product and the gas mixed with the liquid product flows through the exit nozzle, the gas expands and forms bubbles in the liquid product, which creates foam. Once a valve for the canister is opened, however, the pressure drops quickly causing the foam that is generated to lack structure, stability, and consistency. Initially, the foam that is generated may be acceptable for medical use, however, the stability and consistency of the foam will rapidly deteriorate over the course of the dispense, making the foam unreliable and unusable.

There have been some efforts directed to making foam for use in medical procedures. One prior art method for creating foam involves repeatedly passing the surfactant and the gas back and forth between two containers, similar to a syringe exchange, to create enough shear force to agitate the surfactant and the gas to create foam. This methodology, however, is user dependent so that the quality of the foam is impacted by the speed of the passes as well as the number of the passes.

In view of the above-noted problems, there remains a need for improved systems, devices and methods that optimize the sealing characteristics of foam. There is also a need for improved systems, devices and methods that produce foam that stays in place on tissue. In addition, there remains a need for improved systems, devices, and methods for making foam, which create foam at a controllable, predetermined gas to liquid ratio (e.g., 4:1, 2:1), whereby the foam has specific properties including uniform spacing of the gas bubble, stability, and consistency. Moreover, there is a need for improved systems, devices, and methods that do not use flammable liquid propellants, and that lend themselves to a product that can be terminally sterilized.

SUMMARY OF THE INVENTION

In one embodiment, a medical device for making foam preferably includes a syringe including a plunger for dispensing a liquid from a liquid dispensing port, and a mixing chamber including a mixing chamber inlet in fluid communication with the liquid dispensing port, a mixing chamber outlet spaced from the mixing chamber inlet, a liquid flow channel extending between the mixing chamber inlet and the mixing chamber outlet, and a gas inlet channel that intersects with the liquid flow channel for mixing a gas with the liquid dispensed from the liquid dispensing port.

In one embodiment, a medical device for making foam preferably includes a gas cartridge containing an inert gas (e.g., air, carbon dioxide, nitrogen), a first gas conduit having a first end connected with the gas cartridge and a second end connected with the syringe, and a second gas conduit having a first end connected with the gas cartridge and a second end connected with the gas inlet channel of the mixing chamber.

In one embodiment, a medical device for making foam preferably includes an actuator coupled with the gas cartridge for selectively releasing the gas from the gas cartridge for flowing into the first and second gas conduits. In one embodiment, the released gas in the first gas conduit forces the plunger toward the liquid dispensing port for dispensing the liquid from the liquid dispensing port and into the liquid flow channel while the released gas in the second gas conduit flows into the gas inlet channel of the mixing chamber for mixing with the liquid in the liquid flow channel.

In one embodiment, a medical device for making foam preferably includes a check valve disposed between the liquid dispensing port and the mixing chamber inlet that allows the liquid to flow in only one direction from the liquid dispensing port to the mixing chamber inlet while preventing the gas in the gas inlet channel from passing through the check valve.

In one embodiment, a medical device for making foam preferably includes a foaming chamber including a foaming chamber inlet in fluid communication with the mixing chamber outlet, a foaming chamber outlet, and a porous material disposed within the foaming chamber. In one embodiment, the porous material has a tortuous path configured to generate foam as the mixture of the liquid and the gas passes through the porous material. In one embodiment, the porous material in the foaming chamber has a porosity of about 25-40%.

In one embodiment, a medical device for making foam preferably includes one or more regulators for regulating the pressure levels of the gas flowing through the respective first and second gas conduits. In one embodiment, the gas in the first gas conduit and the gas in the second gas conduit have different pressure levels.

In one embodiment, the gas in the gas cartridge is a pressurized gas having a pressure level of about 45-65 pounds per square inch (psi). In one embodiment, the pressurized gas is an inert gas such as air, carbon dioxide and/or nitrogen, and combinations thereof.

In one embodiment, a medical device for making foam preferably includes an end cap secured over a first end of the syringe, whereby the end cap forms an air-tight connection with the first end of the syringe. In one embodiment, the end cap has a gas inlet port, and the first gas conduit is connected with the gas inlet port of the end cap.

In one embodiment, the liquid flow channel has an inner diameter that is about 25-30 times larger than an inner diameter of the gas inlet channel. In one embodiment, the liquid flow channel has an inner diameter of about 0.220 inches and the gas inlet channel has an inner diameter of about 0.008 inches.

In one embodiment, a medical device for making foam preferably includes a syringe including a syringe barrel having a first end, a second end, and a liquid dispensing port located at the second end of the syringe barrel. In one embodiment, a liquid is disposed in the syringe barrel. The liquid may include a surfactant material that facilitates making foam.

In one embodiment, a plunger is disposed within the syringe barrel and is moveable toward the second end of the syringe barrel for dispensing the liquid from the liquid dispensing port.

In one embodiment, a medical device for making foam preferably includes a mixing chamber having a mixing chamber inlet in fluid communication with the liquid dispensing port, a mixing chamber outlet spaced from the mixing chamber inlet, a liquid flow channel extending between the mixing chamber inlet and the mixing chamber outlet, and a gas inlet channel that intersects with the liquid flow channel.

In one embodiment, a medical device for making foam preferably includes a check valve disposed between the liquid dispensing port and the mixing chamber inlet that allows the liquid to flow in only one direction from the liquid dispensing port to the mixing chamber inlet.

In one embodiment, a medical device for making foam preferably includes a gas source including a first gas conduit in fluid communication with the first end of the syringe barrel and a second gas conduit in fluid communication with the gas inlet channel of the mixing chamber.

In one embodiment, a medical device for making foam preferably includes an actuator coupled with the gas source for simultaneously releasing gas from the gas source and into the first and second gas conduits. In one embodiment, the released gas in the first gas conduit forces the plunger toward the second end of the syringe barrel for dispensing the liquid from the liquid dispensing port and into the liquid flow channel while the released gas in the second gas conduit flows through the gas inlet channel of the mixing chamber for mixing with the liquid in the liquid flow channel.

In one embodiment, a medical device for making foam preferably includes a foaming chamber having a foaming chamber inlet in fluid communication with the mixing chamber outlet, a foaming chamber outlet, and a porous material disposed within the foaming chamber. In one embodiment, the mixture of the liquid and the gas passes through the porous material disposed within the foaming chamber for generating foam that is dispensed from the foaming chamber outlet.

In one embodiment, a medical device for making foam preferably includes an end cap secured over the first end of the syringe barrel. In one embodiment, the end cap has a gas inlet port. In one embodiment, the first gas conduit is connected with the gas inlet port of the end cap.

In one embodiment, the liquid flow channel has an inner diameter that is larger than an inner diameter of the gas inlet channel. In one embodiment, the inner diameter of the liquid flow channel is about 25-30 times larger than the inner diameter of the gas inlet channel.

In one embodiment, a medical device for making foam preferably includes at least one regulator for controlling a pressure level of the gas in the first gas conduit and the second gas conduit. In one embodiment, the gas in the first conduit and the gas in the second gas conduit have different pressure levels.

In one embodiment, the gas stored in the gas source is pressurized gas having a pressure level of about 45-65 pounds per square inch. In one embodiment, the pressurized gas is an inert gas such as air, carbon dioxide and/or nitrogen and combinations thereof.

In one embodiment, the porous material in the foaming chamber has a porosity of about 25-40%.

In one embodiment, a medical device for making foam preferably includes a foam collection receptacle connected with the foam chamber outlet for collecting foam generated within the foam chamber.

In one embodiment, a method of making foam used for sealing tissue desirably includes obtaining a container holding a liquid, directing a first stream of a gas toward the container for dispensing a stream of the liquid from the container, simultaneously with directing the first stream of the gas toward the container, directing a second stream of the gas into the dispensed stream of the liquid for generating a liquid and gas mixture, and passing the liquid and gas mixture through a porous material for generating foam.

In one embodiment, a method of making foam includes, prior to directing the first stream of the gas toward the container, introducing a surfactant into the liquid. In one embodiment, a method of making foam includes maintaining the first stream of the gas at a pressure level of about 8-45 pounds per square inch, and maintaining the second stream of the gas at a pressure level of about 65 pounds per square inch.

In one embodiment, a method of making foam includes providing a mixing chamber having a mixing chamber inlet, a mixing chamber outlet, a liquid flow channel extending between the mixing chamber inlet and the mixing chamber outlet, and a gas flow channel that intersects with the liquid flow channel. In one embodiment, a method includes directing the dispensed stream of the liquid into the mixing chamber inlet and through the liquid flow channel, and directing the second stream of the gas into the gas inlet channel of the mixing chamber for introducing the second stream of the gas into the dispensed stream of the liquid.

In one embodiment, a variety of tortuous paths may be used to agitate the liquid/surfactant and create a foam. These embodiments may include glass beads, a POREX filter, and/or mesh screens. In one embodiment, the porosity and the length of the tortuous paths will depend on properties of the liquid product and the desired foam output.

In one embodiment, a single gas inlet channel may be used to introduce the gas into the liquid flow path. In other embodiments, however, systems may use two or more gas inlet channels in order to adjust and/or increase the gas to liquid ratio for creating foam having desired properties. In one embodiment, a mixing chamber may include two or more gas inlet channels for introducing gas into the liquid flow stream passing through the mixing chamber.

In one embodiment, a system for making foam may not require a regulator for regulating the pressure level of a gas. In one embodiment, a system may include an expansion chamber, which allows the regulator to be eliminated. In one embodiment, a system for making foam may eliminate a regulator if the system can handle a continuous drop in pressure without impacting foam consistency and quality. In one embodiment, a system may use house wall pressure (e.g., an on-site gas source) or a carbon dioxide ($CO_2$) tank instead of requiring a gas cartridge.

In one embodiment, a system may function as a two stage or a one stage foaming device. These configurations may be described as a pre-foamer or as an all-in-one device, respectively. The benefit of a pre-foamer is that it allows a user to deliver the foam at his or her own rate. The rate of an all-in-one device would preferably be controlled by the device. This is because the rate of delivery will impact the final foam quality. Both the pre-foamer and all-in-one devices desirably create foam in a single pass through a tortuous path, eliminating the need for multiple passes.

In one embodiment, a system for making foam isolates the surfactant from the gas during product storage. In one embodiment, isolating the surfactant from the gas preferably eliminates the need for a liquid propellant, which eliminates sterilization challenges and potential flammability concerns.

In one embodiment, a system for making foam allows the gas and the liquid to be tuned/regulated individually, which allows for simple changes to the system to target different gas to liquid ratios for the foam output.

In one embodiment, a device for creating foam preferably includes a syringe or cartridge that contains a liquid. In one embodiment, the liquid may include a surfactant (i.e., foaming) material.

In one embodiment, the liquid with the surfactant material may be dispensed using pressurized gas and/or a spring that depresses a plunger.

In one embodiment, the pressurized gas may be generated using either a gas cartridge or manually by a user utilizing a larger syringe.

In one embodiment, a one-way check valve may prevent the backflow of a pressurized gas into the surfactant syringe.

In one embodiment, a system may include a mixing chamber where the surfactant and the gas are introduced.

In one embodiment, a system may include a method for activating the flow of the surfactant material and the gas (e.g., a push button valve).

In one embodiment, the mixture of the gas and the liquid may be passed through a porous material that defines a tortuous path for generating the foam.

Unlike traditional gas canisters, which have both surfactant and gas in a single container, in one embodiment, the systems, devices and methods disclosed herein teach isolating the gas and the liquid in separate containers. This provides a number of benefits including 1) the gas to liquid ratio that is present in the foam may be regulated by constricting the gas inlet channel and/or the liquid flow channel. Refining the gas to liquid ratio may be desirable for obtaining desired mechanical properties in the foam; 2) isolating the liquid in a plunger driven container allows the system to be used in any orientation by the user, unlike traditional gas canister systems; 3) pressurized vessel are typically metallic and difficult to irradiate. By removing the liquid/surfactant from the pressurized vessel, the liquid/surfactant may be placed within a glass or plastic container (e.g., syringe), which could be radiation sterilized; 4) both the liquid syringe and the gas introduced in the mixing chamber are driven by controlled pressure sources, which minimizes the influence of user variability.

These and other preferred embodiments of the present invention will be described in more detail below.

BRIEF DESCRIPTION OF THE DRAWINGS

FIG. 1A shows a schematic view of a system for making foam used in medical procedures, in accordance with one embodiment of the present patent application.

DETAILED DESCRIPTION OF PREFERRED EMBODIMENTS

Figure 1B:
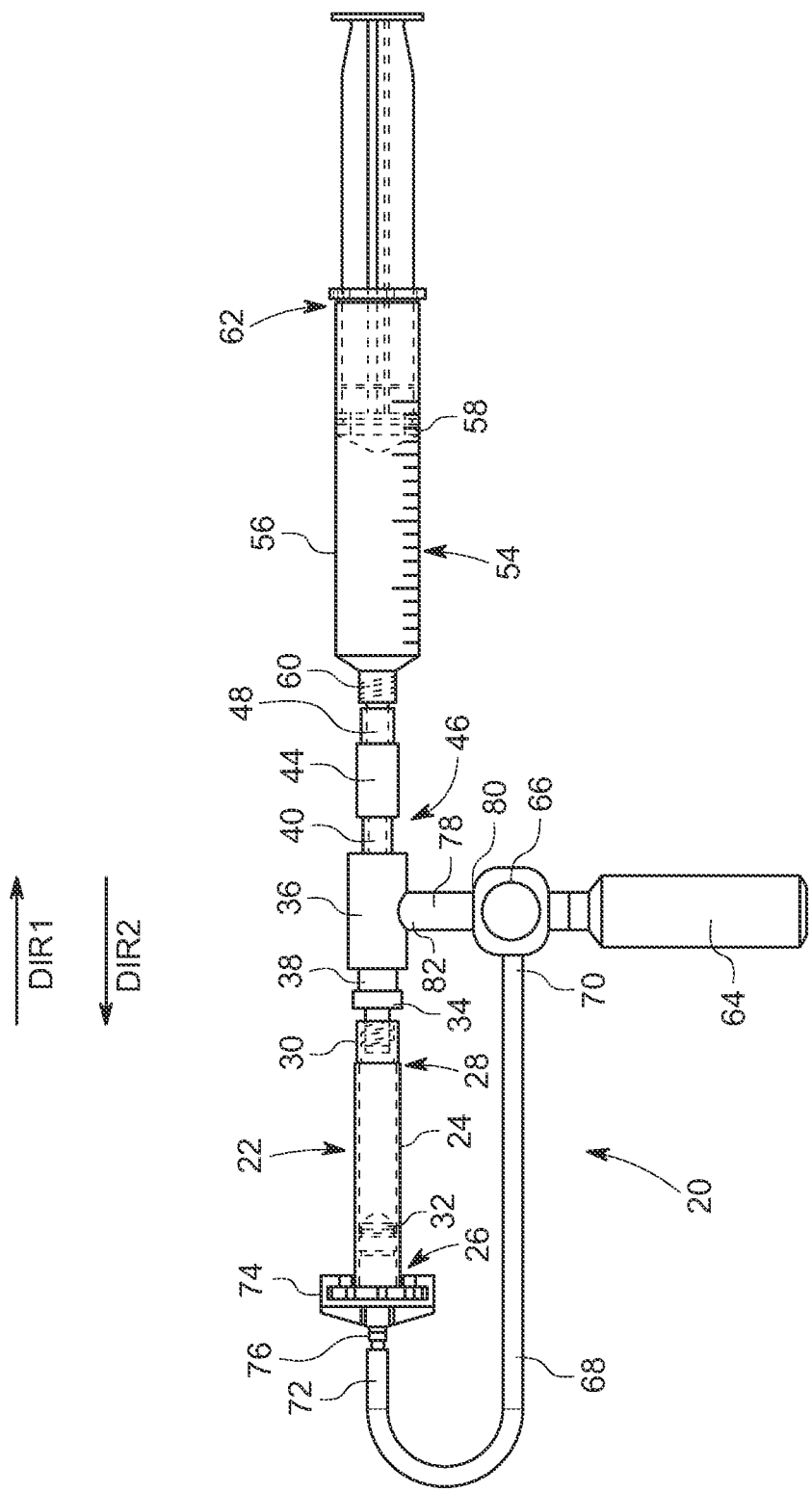
FIG. 1B shows a system for making foam used in medical procedures including a gas cartridge, a liquid syringe, a check valve, a mixing chamber, a foaming chamber, and a foam transfer receptacle, in accordance with one embodiment of the present patent application.

Referring to FIGS. 1A and 1B, in one embodiment, a system 20 for making foam used in medical procedures preferably includes a syringe 22. The syringe may be filled with a liquid used for making foam. In one embodiment, the syringe 22 may include a syringe barrel 24 having a first end 26, a second end 28, and a liquid dispensing port 30 located at the second end of the syringe barrel. In one embodiment, the syringe 22 desirably includes a plunger 32 that is disposed within the syringe barrel 24. In one embodiment, the plunger 32 is configured to reciprocate back and forth between moving in a first direction toward the first end 26 of the syringe barrel 24 for drawing a liquid into the syringe barrel, and moving in an opposite, second direction toward the second end 28 of the syringe barrel 24 for dispensing a liquid from the liquid dispensing port 30 located at the second end 28 of the syringe barrel 24. In one embodiment, the plunger 32 has an outer perimeter that preferably forms a water-tight and/or air-tight seal with an inner surface of the syringe barrel 24 so that liquid and gas may not pass between the outer perimeter of the plunger and the inner surface of the syringe barrel.

In one embodiment, the syringe 22 may be filled with a liquid that is used for making foam. In one embodiment, a gas may be introduced into and/or mixed with the liquid for generating the foam. In one embodiment, the liquid may contain a surfactant, which is a substance that can reduce the surface tension of a liquid and thus allow it to foam. See https://www.collinsdictionary.com/us/dictionary/english/surfactant.

In one embodiment, the system 20 for making foam preferably includes a one-way check valve 34 that is coupled with the liquid dispensing port 30 at the second end 28 of the syringe barrel 24. The one-way check valve 34 preferably enables liquid dispensed from the syringe barrel to move downstream in the direction indicated DIR1, however, after the liquid has entered the one-way check valve 34, the check valve prevents the liquid from reversing direction and moving upstream in the direction DIR2. In one embodiment, the check valve 34 also desirably prevents any gas that is present in the system from passing through the check valve and entering the liquid dispensing port 30.

In one embodiment, the system 20 for making foam preferably includes a mixing chamber 36 having a mixing chamber inlet 38 and a mixing chamber outlet 40. In one embodiment, after the liquid dispensed from the syringe barrel 24 passes through the one-way check valve 34, the dispensed liquid enters the mixing chamber inlet 38 of the mixing chamber 36 where it is mixed with a gas that is introduced into the mixing chamber for making foam.

In one embodiment, the mixing chamber 36 preferably includes a gas inlet 42 that is located between the mixing chamber inlet 38 and the mixing chamber outlet 40. In one embodiment, gas (e.g., air, carbon dioxide, nitrogen) is introduced into the mixing chamber via the gas inlet 42 for being mixed with the stream of the liquid that is passing through the mixing chamber 36. The gas introduced into the mixing chamber 36 may be compressed so that it has a higher pressure level than atmosphere and/or ambient air.

In one embodiment, the system 20 for making foam desirably includes a foaming chamber 44 having a foaming chamber inlet 46 and a foaming chamber outlet 48. In one embodiment, the foaming chamber inlet 46 is coupled with the mixing chamber outlet 40 for receiving the liquid and gas mixture that has been joined together within the mixing chamber 36. In one embodiment, the foaming chamber 44 preferably contains a porous material 50 that provides a tortuous path through which the liquid and gas mixture passes for generating foam. In one embodiment, after the liquid and gas mixture passes through the foaming chamber 44, a foam 52 is preferably dispensed from the foaming chamber outlet 48 of the foaming chamber.

In one embodiment, the porous material desirably has a porosity of 25-50% and more preferably about 30-35%. As used herein the term porosity is defined as a measure of the void space in a material, and is a fraction of the volume of the voids in the material over the total volume of the material. In one embodiment, the porous material 50 may be one or more blocks of porous material sold under the trademark POREX by Porex Corporation of Fairburn, Ga. The one or more blocks of porous material may be packed into the foaming chamber. In other embodiments, the porous material may include glass beads packed inside the foaming chamber, or a mesh material disposed inside the foaming chamber.

Referring to FIG. 1B, in one embodiment, the system 20 for making foam preferably includes a foam transfer receptacle 54 that collects the foam that has been generated by the system. In one embodiment, the foam transfer receptacle desirably includes a syringe barrel 56 with a plunger 58 disposed inside the syringe barrel 56. In one embodiment, the foam transfer receptacle 54 preferably includes a foam collection opening 60 that is adapted to be coupled with the foaming chamber outlet 48 for transferring the foam generated within the foaming chamber 44 to the syringe barrel 56 of the foam transfer receptacle 54. In one embodiment, the plunger 58 is retracted toward the first end 62 of the syringe barrel 56 for drawing the foam through the foam collection opening 60 and into the syringe barrel 56 of the foam transfer receptacle 54. In one embodiment, the syringe barrel 56 of the foam collector receptacle 54 may include one or more vents, small holes, and/or small openings for relieving pressure inside the syringe barrel as the gas is activated.

Referring to FIGS. 1A and 1B, in one embodiment, the system 20 for making foam preferably includes a supply of gas. In one embodiment, the gas is pressurized gas that is provided in a gas cartridge 64 that contains the pressurized gas. In one embodiment, the pressurized gas is an inert gas such as air, carbon dioxide, and nitrogen. In one embodiment, the pressurized gas has a pressure level that is greater than ambient air. In one embodiment, the pressurized gas may be pressurized to a pressure level within the range of about 65-85 pounds per square inch (psi).

In one embodiment, the system 20 for making foam preferably includes an actuator 66 that may be engaged for releasing the pressurized gas from the gas cartridge 64. In one embodiment, the actuator 66 may be a push button. In other embodiments, the actuator may be a trigger, a switch, and/or a valve that may be moved between an opened position for releasing the gas from the cartridge and a closed position preventing the release of the gas from the cartridge.

In one embodiment, the system 20 for making foam preferably includes a first gas conduit 68 having a first end 70 in fluid communication with the gas cartridge 64 and a second end 72 in fluid communication with the first end 26 of the syringe barrel 24. In one embodiment, an end cap 74 is secured over the first end 26 of the syringe barrel 24 to form an air-tight fit with the first end 26 of the syringe barrel 24. In one embodiment, the end cap 74 desirably includes a gas inlet port 76 that is coupled with the second end 72 of the first gas conduit 68 so that the pressurized gas may be selectively directed into the first end of the syringe barrel 24.

In one embodiment, when the actuator 66 is engaged for releasing pressurized gas from the gas cartridge 64, at least some of the pressurized gas passes through the first gas conduit 68 for passing into the first end 26 of the syringe barrel 24 to force the plunger 32 toward the second end 28 of the syringe barrel 24. As the plunger 32 is forced by the pressurized gas toward the second end 28 of the syringe barrel 24, the liquid within the syringe barrel 24 is forced out of the liquid dispensing port 30 of the syringe barrel and into the one-way check valve 34. In one embodiment, the system may include a regulator (not shown) for controlling the pressure level of the gas that flows through the first gas conduit and into the first end of the syringe barrel. In one embodiment, the pressure level of the gas within the first gas conduit is about 40-50 psi and more preferably about 45 psi. The pressure level of the gas may be modified depending on numerous variable including the size (e.g., diameter) of the syringe barrel and the length and/or inner diameter of the first gas conduit.

In one embodiment, the system 20 for making foam preferably includes a second gas conduit 78 that extends between the gas cartridge 64 and the mixing chamber 36. In one embodiment, the second gas conduit 78 preferably has a first end 80 that may be placed in fluid communication with the pressurized gas within the gas cartridge 64 and a second end 82 that is in fluid communication with the gas inlet 42 of the mixing chamber 36. In one embodiment, when the actuator 66 is engaged for releasing pressurized gas from the gas cartridge 64, at least some of the pressurized gas passes through the second gas conduit 78 and into the gas inlet 42 of the mixing chamber 36, where the gas stream intersects and/or is injected into the stream of the liquid that has been dispensed from the syringe barrel 24 and that is flowing through the mixing chamber 36. After the pressurized gas in the second gas conduit 78 has been mixed with the stream of liquid flowing through the mixing chamber 36, the mixture of the liquid and the pressurized gas exits the mixing chamber via the mixing chamber outlet for being introduced into the foaming chamber 44.

In one embodiment, the system may include a regulator (not shown) for controlling the pressure level of the gas that flows through the second gas conduit 78 and into the mixing chamber 36. In one embodiment, the pressure level of the gas within the second gas conduit is about 60-70 psi and more preferably about 65 psi. The pressure level of the gas may be modified depending on numerous variable including the size (e.g., inner diameter) of the gas inlet into the mixing chamber and the length and/or inner diameter of the second gas conduit.

In one embodiment, after the actuator 66 has been engaged for releasing the pressurized gas from the gas cartridge 64, the pressurized gas moves simultaneously through both the first gas conduit 68 and the second gas conduit 78 for simultaneously driving the plunger 32 toward the second end 28 of the syringe barrel 24 (to dispense the liquid) and forcing pressurized gas into the mixing chamber 36 for mixing gas with the stream of liquid that has been dispensed from the syringe barrel 24. As noted above, the system may include one or more regulators for controlling the pressure and/or the volume of the pressurized gas that flows through the respective first and second gas conduits 68, 78. The specific pressure levels that are utilized are designed to synchronize the dispensing of the liquid with the mixing of the gas into the dispensed liquid to provide a consistent environment for making foam. In one embodiment, the system may include a splitter for splitting the pressurized gas into the first gas conduit and the second gas conduit.

Figure 2:
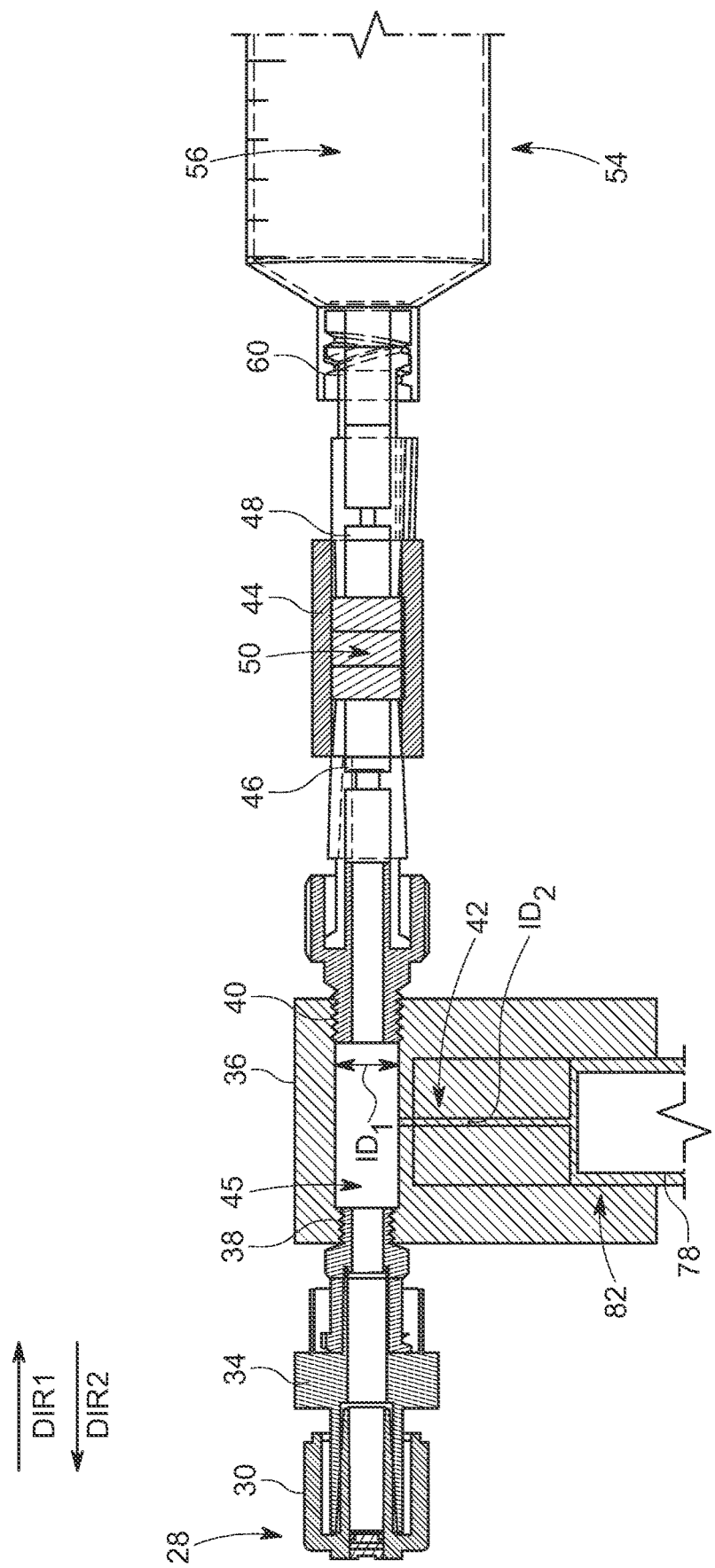
FIG. 2 shows a cross-sectional view of the check valve, the mixing chamber, the foaming chamber, and the foam transfer receptacle shown in FIG. 1B.

Referring to FIG. 2, in one embodiment, the liquid dispensing port 30 at the second end 28 of the syringe barrel 24 (FIG. 1B) is coupled with the one-way check valve 34. The one-way check valve 34 allows the liquid dispensed from the liquid dispensing port 30 at the second end of the syringe barrel 24 to move downstream in the direction designated DIR1, but prevents the liquid or gas from moving upstream in a direction designated DIR2 once it reaches the one-way check valve 34. The check valve 34 is in fluid communication with the mixing chamber inlet 38, whereby the mixing chamber receives the liquid after it passes through the check valve 34. The mixing chamber 36 desirably includes the mixing chamber inlet 38, the mixing chamber outlet 40 and a liquid flow channel 45 that extends between the mixing chamber inlet 38 and the mixing chamber outlet 40 for directing the liquid through the mixing chamber. The mixing chamber 36 preferably includes the gas inlet 42 that intersects with the liquid flow channel 45 for introducing and/or injecting the pressurized gas into the stream of liquid as it flows through the liquid flow channel 45. In one embodiment, the second end 82 of the second gas conduit 78 (FIG. 1B) is coupled with the mixing chamber 36 for directing the pressurized gas into the gas inlet 42.

In one embodiment, the inner diameter of the gas inlet 42 is smaller than the inner diameter of the liquid flow channel 45. In one embodiment, the liquid flow channel 45 preferably has an inner diameter $ID_1$ of about 0.22 inches. In one embodiment, the gas inlet 42 has an inner diameter $ID_2$ of about 0.008 inches. The inner diameters of the respective liquid flow channel 45 and gas inlet 42 may be modified to adjust the gas to liquid ratio that used within the mixing chamber for controlling the type of foam that is produced. In one embodiment, the foam has a gas to liquid ratio of about 4:1.

In one embodiment, the pressurized gas directed through the first and second gas conduits 68, 78 preferably has a pressure level of about 45-65 psi. In one embodiment, the pressure level of the pressurized gas within the first gas conduit 68 is about 65 psi, and the pressure level of the pressurized gas within the second gas conduit 78 is about 45 psi.

In one embodiment, the liquid syringe may be a 20 mL BD syringe. In this embodiment, the pressure of the gas in the first gas conduit used to push the plunger within the liquid syringe was about 8-12 psi, and the pressure of the gas introduced into the mixing chamber through the second gas conduit was about 65-85 psi.

In one embodiment, the liquid syringe may be a 3 mL Nordson syringe. In this embodiment, the pressure of the gas in the first gas conduit used to push the plunger within the liquid syringe was about 30-50 psi, and the pressure of the gas introduced into the mixing chamber through the second gas conduit was about 65 psi.

In one embodiment, the foaming chamber 44 is located downstream of the mixing chamber outlet 40. In one embodiment, the foaming chamber 44 has a foaming chamber inlet 46 that is coupled with the mixing chamber outlet 40 so that the liquid and the pressurized gas mixed together within the mixing chamber 36 is passed into the foaming chamber 44. In one embodiment, the foaming chamber 44 desirably includes porous material 50 that provides a tortuous path for the liquid and gas mixture as it moves downstream between the foaming chamber inlet 46 and the foaming chamber outlet 48. In one embodiment, the porous material 50 has a porosity of 30-35%. As the liquid and gas mixture passes through the porous material 50, the mixture transforms into a foam that is introduced into the syringe barrel 56 of a foam transfer receptacle 54 via a coupling between the foaming chamber outlet 48 and the foam collection port 60 of the foam transfer receptacle 54.

In one embodiment, a system for making foam may include two separate liquids that are mixed together, whereby a gas is then introduced into a stream of the two mixed liquids for making the foam. The two liquids that are mixed together may have different properties. For example, one of the liquids may include a surfactant and one of the liquids may include a cross-linker.

Figure 3A:
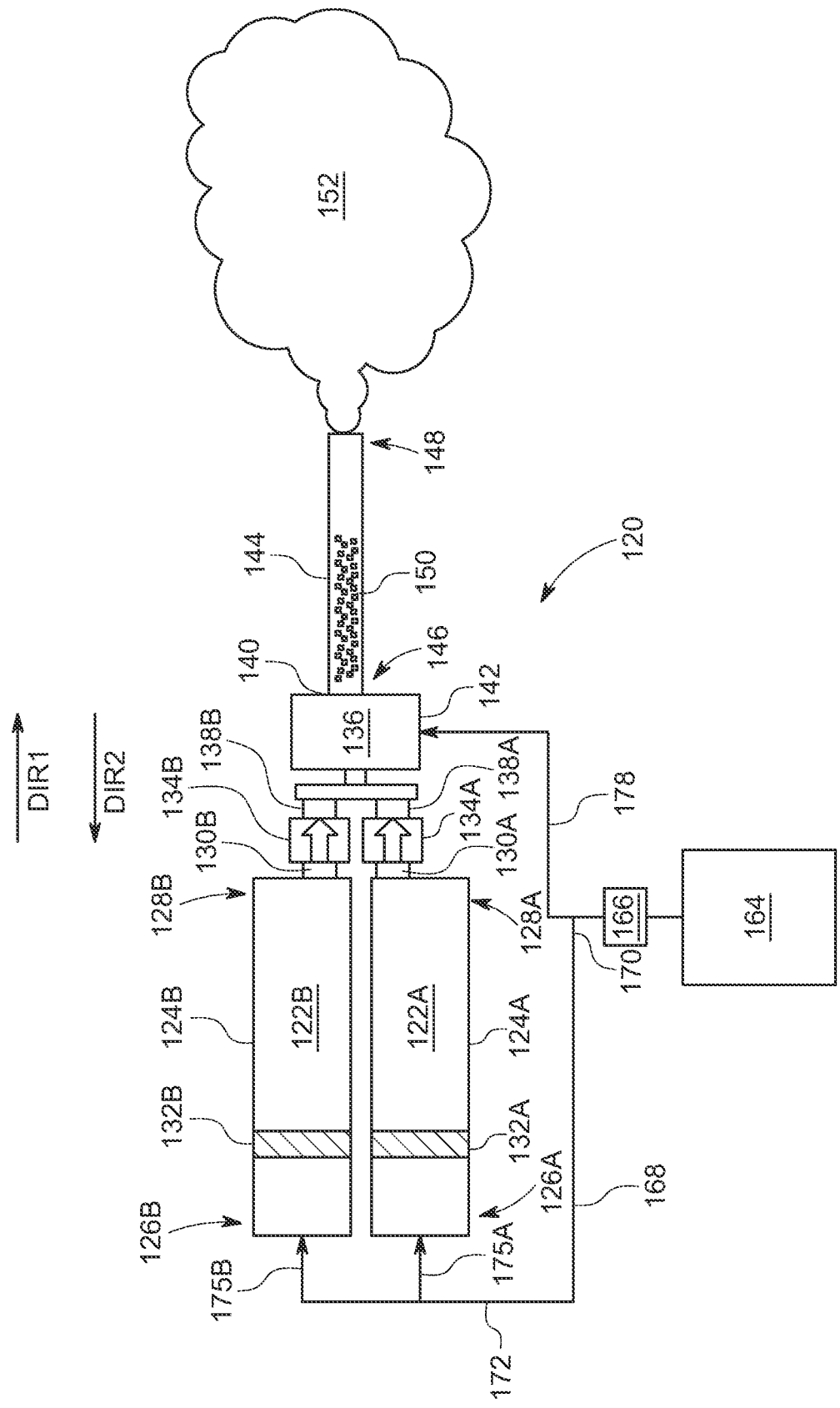
FIG. 3A shows a schematic view of a system for making foam used in medical procedures, which is made using a two part liquid product, in accordance with one embodiment of the present patent application.
Figure 3B:
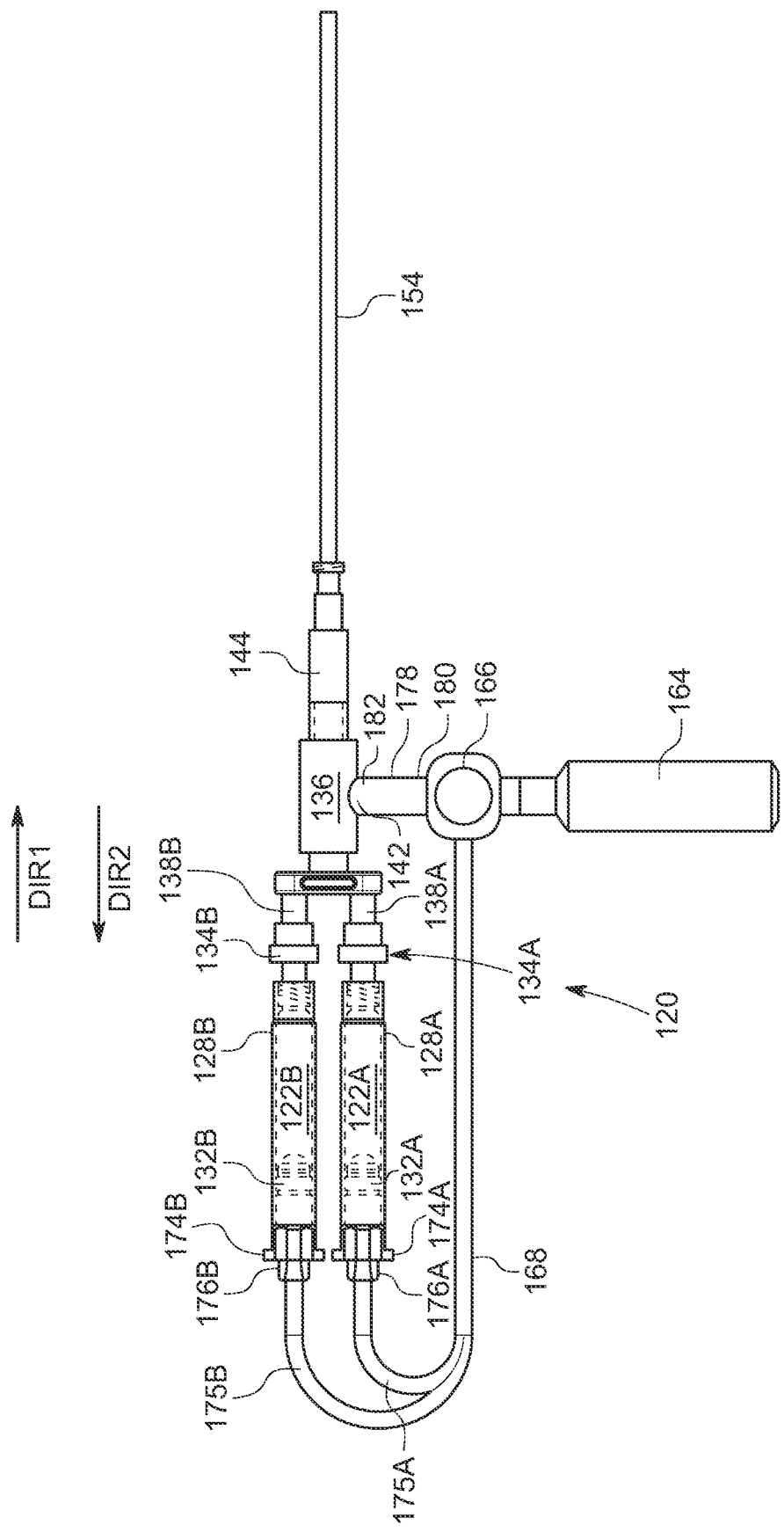
FIG. 3B shows a system for making foam used in medical procedures including a gas cartridge, first and second liquid syringes, first and second check valves, a mixing chamber, a foaming chamber, and a foam delivery shaft, in accordance with one embodiment of the present patent application.

Referring to FIGS. 3A and 3B, in one embodiment, a system 120 for making foam used in medical procedures preferably includes a first syringe 122A, which may be filled with a first liquid that is used for making foam. In one embodiment, the first syringe 122A may include a first syringe barrel 124A having a first end 126A, a second end 128A, and a first liquid dispensing port 130A located at the second end of the first syringe barrel. In one embodiment, the first syringe 122A desirably includes a first plunger 132A that is disposed within the first syringe barrel 124A. In one embodiment, the first plunger 132A is configured to reciprocate back and forth between moving in a first direction toward the first end 126A of the syringe barrel 124A for drawing a liquid into the first syringe barrel, and moving in an opposite, second direction toward the second end 128A of the first syringe barrel 124A for dispensing a liquid from the liquid dispensing port 130A located at the second end 128A of the first syringe barrel 124A. In one embodiment, the first plunger 132A has an outer perimeter that preferably forms a water-tight and/or an air-tight seal with an inner surface of the first syringe barrel 124A.

In one embodiment, the system 120 for making foam preferably includes a first one-way check valve 134A that is coupled with the first liquid dispensing port 130A at the second end 128A of the first syringe barrel 124A. The first one-way check valve 134A preferably enables liquid dispensed from the syringe barrel to move downstream in the direction indicated DIR1, however, after the liquid has entered the first one-way check valve 134A, the check valve prevents the liquid or a gas from reversing direction and moving upstream in the direction DIR2.

In one embodiment, a system 120 for making foam used in medical procedures preferably includes a second syringe 122B, which may be filled with a second liquid that is used for making foam. In one embodiment, the second syringe 122B may include a second syringe barrel 124B having a first end 126B, a second end 128B, and a second liquid dispensing port 130B located at the second end of the second syringe barrel. In one embodiment, the second syringe 122B desirably includes a second plunger 132B that is disposed within the second syringe barrel 124B. In one embodiment, the second plunger 132B is configured to reciprocate back and forth between moving in a first direction toward the first end 126B of the second syringe barrel 124B for drawing a liquid into the second syringe barrel, and moving in an opposite, second direction toward the second end 128B of the second syringe barrel 124B for dispensing a liquid from the liquid dispensing port 130B located at the second end 128B of the second syringe barrel 124B. In one embodiment, the second plunger 132B has an outer perimeter that preferably forms a water-tight and/or an air-tight seal with an inner surface of the second syringe barrel 124B.

In one embodiment, the system 120 for making foam preferably includes a second one-way check valve 134B that is coupled with the second liquid dispensing port 130B at the second end 128B of the second syringe barrel 124B. The second one-way check valve 134B preferably enables liquid dispensed from the second syringe barrel 124B to move downstream in the direction indicated DIR1, however, after the liquid has entered the second one-way check valve 134B, the check valve prevents the liquid or a gas from reversing direction and moving upstream in the direction DIR2.

In one embodiment, the system 120 for making foam preferably includes a mixing chamber 136 having a first mixing chamber inlet 138A for receiving the first liquid from the first liquid syringe 122A, and a second mixing chamber inlet 138B for receiving the second liquid from the second liquid syringe 122B. In one embodiment, the first and second liquids are desirably joined together into a single liquid stream prior to entering the mixing chamber. In one embodiment, the mixing chamber 136 has a mixing chamber outlet 140. In one embodiment, after the first and second liquids are dispensed from the respective first and second syringe barrels 124A, 124B and enter the mixing chamber 136, the first and second liquid streams are joined together and are mixed with a gas (e.g., a pressurized gas) for making foam, as will be described in more detail herein. In one embodiment, the ratio of the gas to the two liquids that are mixed together in the mixing chamber may be about 2:1.

In one embodiment, the mixing chamber 136 preferably includes a gas inlet 142 that is located between the mixing chamber inlets 138A, 138B and the mixing chamber outlet 140. In one embodiment, gas (e.g., air, carbon dioxide, nitrogen) is introduced into the mixing chamber via the gas inlet 142 for being mixed with and/or injected into the stream of the joined first and second liquids passing through the mixing chamber 136. The gas may be compressed so that it has a higher pressure level than atmosphere and/or ambient air.

In one embodiment, the system 10 for making foam desirably includes a foaming chamber 144 having a foaming chamber inlet 146 and a foaming chamber outlet 148. In one embodiment, the foaming chamber inlet 146 is coupled with the mixing chamber outlet 140 for receiving the liquid and gas mixture that is joined together within the mixing chamber 136. In one embodiment, the foaming chamber 144 preferably contains a porous material 150 that provides a tortuous path through which the liquid and gas mixture passes for generating foam. In one embodiment, the porous material 150 may be a porous material sold under the trademark POREX by Porex Corporation of Fairburn, Ga. In other embodiments, the porous material may include glass beads packed inside the foaming chamber, or a mesh material disposed inside the foaming chamber. In one embodiment, after the liquid and gas mixture passes through the foaming chamber 144, a foam 152 is preferably dispensed from the foaming chamber outlet 148 of the foaming chamber.

In one embodiment, the system 120 for making foam preferably includes a foam delivery shaft 154 (FIG. 3B) that directly dispenses the foam that has been created by the system. In one embodiment, the foam delivery shaft 154 may be elongated and may have an opening at a second end 155 for directly dispensing the foam onto tissue at a surgical site.

In one embodiment, the system 120 for making foam preferably includes a supply of pressurized gas such as a gas cartridge 164 that contains the pressurized gas. In one embodiment, the pressurized gas is an inert gas such as air, carbon dioxide, and nitrogen. In one embodiment, the pressurized gas has a pressure level that is greater than ambient air. In one embodiment, the pressurized gas may be pressurized to a pressure level within the range of about 65-85 psi. The system may include one or more regulators for regulating the pressure level of the pressurized gas.

In one embodiment, the system 120 for making foam preferably includes an actuator 166 that may be engaged for releasing the pressurized gas from the gas cartridge 164. In one embodiment, the actuator 166 may be a push button. In other embodiments, the actuator may be a trigger, a switch, and/or a valve that may be moved between open and closed positions.

In one embodiment, the system 120 for making foam preferably includes a first gas conduit 168 having a first end 170 in fluid communication with the gas cartridge 164 and a second end 172 that splits into a first branch 175A that is in fluid communication with the first end 126A of the first syringe barrel 124A and a second branch 175B that is in fluid communication with the first end 126B of the second syringe barrel 124B.

Referring to FIG. 3B, in one embodiment, a first end cap 174A is secured over the first end 126A of the first syringe barrel 124A to form an air-tight fit with the first end 126A of the first syringe barrel 124A. In one embodiment, the first end cap 124A desirably includes a first gas inlet port 176A that is coupled with the second end 172A of the first branch 175A of the first gas conduit 168 so that the pressurized gas may be selectively directed into the first end of the first syringe barrel 124A.

In one embodiment, a second end cap 174B is secured over the first end 126B of the second syringe barrel 124B to form an air-tight fit with the first end 126B of the second syringe barrel 124B. In one embodiment, the second end cap 124B desirably includes a second gas inlet port 176B that is coupled with the second end 172B of the second branch 175B of the first gas conduit 168 so that the pressurized gas may be selectively directed into the first end of the second syringe barrel 124B.

In one embodiment, when the actuator 166 is engaged for releasing pressurized gas from the gas cartridge 164, at least some of the pressurized gas passes through the first gas conduit 68 and flows into the first and second branches 175A, 175B for forcing the first plunger 132A toward the second end 128A of the first syringe barrel 124A and the second plunger 132B toward the second end 128B of the second syringe barrel 124B. As the first and second plungers 132A, 132B are forced by the pressurized gas toward the second ends 128A, 128B of the respective first and second syringe barrels 124A, 124B, the first and second liquids within the respective first and second syringe barrels 124A, 124B are forced out of the first and second liquid dispensing ports 130A, 130B of the respective first and second syringe barrels and through the respective one-way check valves 134A, 134B.

In one embodiment, the system 120 for making foam preferably includes a second gas conduit 178 that extends between the gas cartridge 164 and the mixing chamber 136. In one embodiment, the second gas conduit 178 preferably has a first end 180 that may be placed in fluid communication with the pressurized gas within the gas cartridge 164 and a second end 182 that is in fluid communication with the gas inlet 142 of the mixing chamber 136. In one embodiment, when the actuator 166 is engaged for releasing pressurized gas from the gas cartridge 164, at least some of the pressurized gas passes through the second gas conduit 178, and through the gas inlet 142 of the mixing chamber 136, where it intersects with and/or is injected into the stream of the first and second liquids that have been dispensed from the respective first and second syringes 122A, 122B. After the pressurized gas in the second gas conduit 178 has been mixed with the stream of the first and second liquids in the mixing chamber 136, the mixture of the liquids and the pressurized gas exits the mixing chamber via the mixing chamber outlet for being introduced into the foaming chamber 144.

In one embodiment, after the actuator 166 has been engaged for releasing the pressurized gas in the gas cartridge 164, the pressurized gas moves simultaneously through both the first gas conduit 168 and the second gas conduit 178 for simultaneously driving the first and second plungers 132A, 132B toward the second ends 128A, 128B of the respective first and second syringe barrels 124A, 124B (to dispense the first and second liquids) and forcing pressurized gas into the mixing chamber 136 for mixing the liquids dispensed from the first and second syringe barrels 124A, 124B with the gas dispensed from the gas cartridge 164. The system may include regulators for controlling the pressure and/or the volume of the pressurized gas that flows into the respective first and second gas conduits 168, 178. The system may include a splitter for splitting the pressurized gas into the first gas conduit and the second gas conduit. In one embodiment, a single source of pressurized gas is used to simultaneously force the first and second plungers 132A, 132B within the respective first and second syringes 122A, 122B toward the second ends of the syringe barrels for dispensing the first and second liquids while some of the pressurized gas is mixed into the stream of the two dispensed liquids for generating foam.

Figure 4:
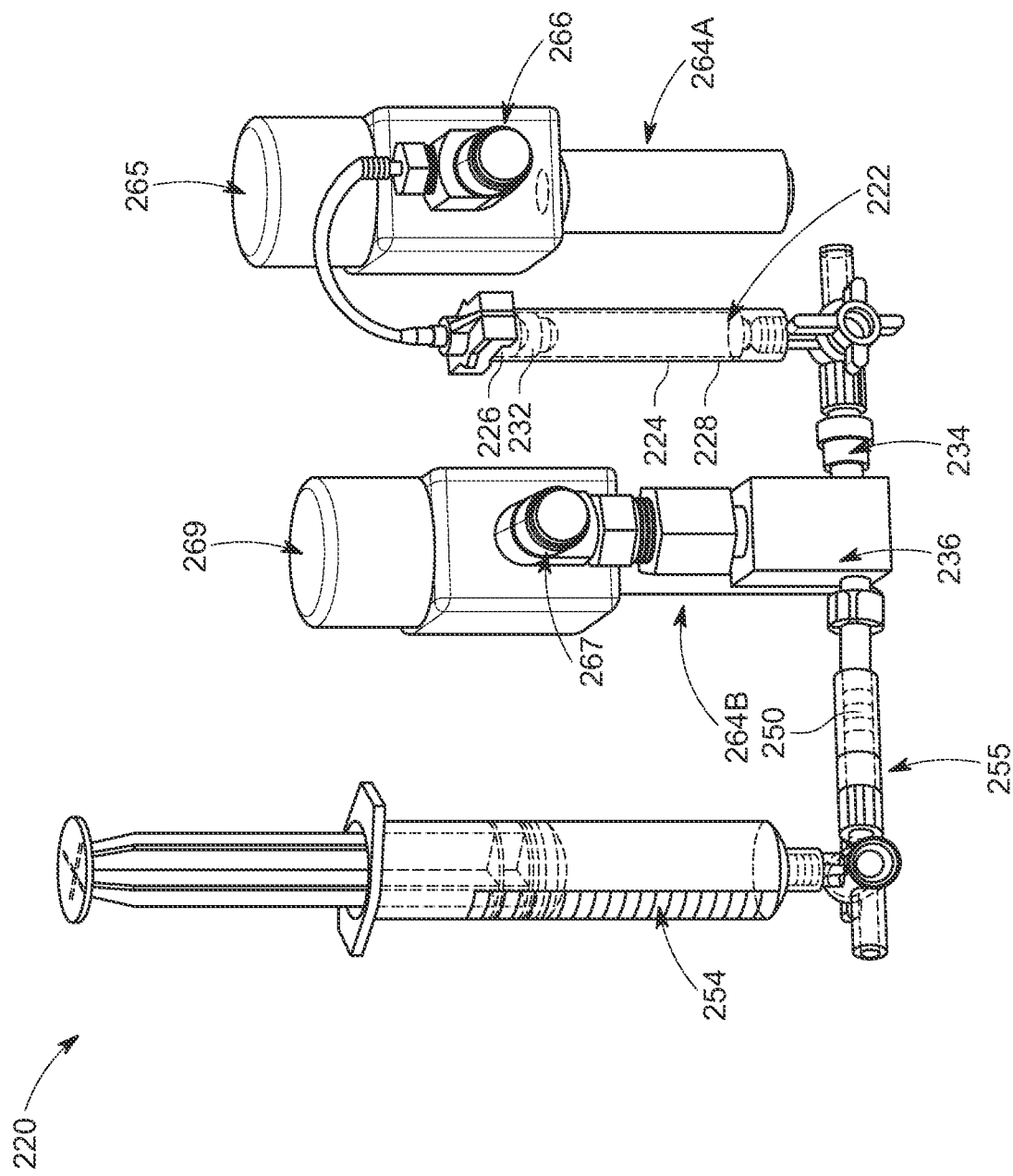
FIG. 4 shows a system for making foam used in medical procedures, the system including a mixing chamber, in accordance with one embodiment of the present patent application.

In one embodiment, a first source of pressurized gas may be used for dispensing a liquid, and a second source of pressurized gas, separate from the first source of pressurized gas, may be mixed with the dispensed liquid(s) for making foam. Referring to FIG. 4, in one embodiment, a system 220 for making foam used in medical procedures preferably includes a liquid syringe 222 having a plunger 232 that is adapted to move toward a second end 228 of a syringe barrel 224 for dispensing a liquid from the liquid syringe 222. In one embodiment, the system 220 preferably includes a first gas cartridge 264A having a push button actuator 266 for releasing a first pressurized gas stored in the first gas cartridge 264A. In one embodiment, a first gas regulator 265 controls the pressure level of the first pressurized gas that is dispensed from the first gas cartridge 264A. In one embodiment, the system 220 preferably includes a first gas conduit 268 that directs the first pressurized gas from the first gas cartridge 264A into a first end 226 of the syringe barrel 224 of the liquid syringe 222 for forcing the plunger 232 to move toward the second end 228 of the syringe barrel 224 for dispensing the liquid from the syringe barrel 224.

In one embodiment, the system 220 for making foam preferably includes a one-way check valve 234 that allows the liquid dispensed from the liquid syringe 222 to pass into a mixing chamber 236. After the liquid has been dispensed from the liquid syringe 222, the one-way check valve 234 allows the liquid to move in only one direction (i.e., toward the mixing chamber) and not reverse direction for flowing back into the liquid syringe 222.

In one embodiment, the system 220 desirably includes a second gas cartridge 264B that contains a second pressurized gas that may be dispensed by engaging an actuator button 267. The system 220 preferably includes a second gas regulator 269 that regulates the pressure level of the second pressurized gas released by the second gas cartridge 264B. In one embodiment, when the second actuator 267 is engaged, the second pressurized gas in the second gas cartridge 264B enters into the mixing chamber 236 where it is mixed with and/or injected into the liquid dispensed from the liquid syringe 222.

In one embodiment, it is desirably to control the ratio of the gas and the liquid for making foam having desired properties such as foam having preferred gas bubble size, gas bubble consistency, gas bubble spacing, etc. In one embodiment, the ratio of the gar to liquid is about 4:1 and may be controlled by adjusting the size of the liquid syringe, the size of the liquid and gas flow channels, the length and inner diameters of liquid and gas conduits, and the pressure levels used for dispensing liquids and injecting gas into the liquids.

After the liquid and the second pressurized gas mixture from the gas cartridge 264B has been joined together in the mixing chamber 236, the mixture of liquid and pressurized gas desirably moves downstream where it enters the foaming chamber 244 having the porous material 250. The porous material 250 provides a tortuous path for the mixture of the liquid and the second pressurized gas for forming a foam that is discharged from the foaming chamber 244 for introduction into a foam transfer receptacle 254 that collects the foam.

In the embodiment shown in FIG. 4, the first pressurized gas from the first gas cartridge 264A forces the plunger 232 toward the second end 228 of the liquid syringe barrel 224, and the second pressurized gas from the second gas cartridge 264B is introduced into the liquid flowing through the mixing chamber 236. In one embodiment, the actuators 266, 267 may be engaged simultaneously so that the plunger 232 is forced toward the second end 228 of the syringe barrel 224 as the second pressurized gas from the second gas cartridge 264B is introduced into the mixing chamber 236. The first and second actuators may be joined together via a structural connection or via an electronic circuit to insure simultaneous activation.

Figure 5:
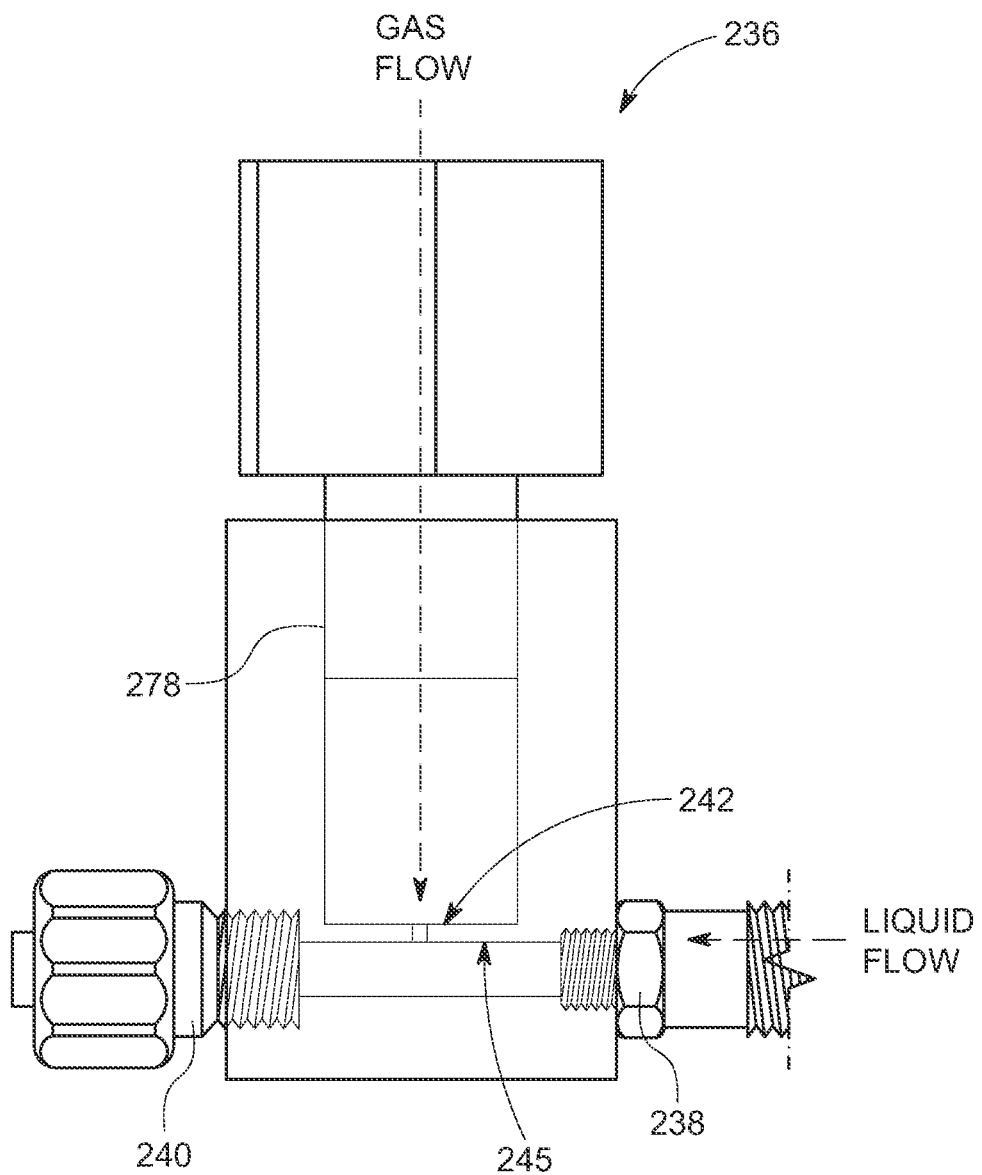
FIG. 5 shows a transparent view of the mixing chamber shown in FIG. 4.

Referring to FIGS. 4 and 5, in one embodiment, the mixing chamber 236 is configured to mix the liquid from the liquid syringe 222 with the second pressurized gas from the second gas cartridge 264B. In one embodiment, the mixing chamber 236 preferably includes the mixing chamber inlet 238 that is adapted to receive the liquid from the liquid syringe 222 and a mixing chamber outlet 240 that is adapted to dispense the liquid after it has been mixed with the second pressurized gas from the second gas cartridge 264B.

Referring to FIG. 4, in one embodiment, the speed at which the plunger 232 moves in the liquid syringe 222 that contains the liquid is driven by a set pressure on the first gas regulator 265. In one embodiment, the pressure level of the gas is introduced into the mixing chamber 236 is driven by a set pressure on the second gas regulator 269. In one embodiment, the first actuator 266 starts and stops the flow of the liquid and the second actuator 267 starts and stops the flow of the gas into the mixing chamber. In one embodiment, the gas that is directed into the mixing chamber enters the mixing chamber before the liquid enters the mixing chamber.

In one embodiment, the mixing chamber 236 is designed to allow for a specific interaction between the gas and liquid/surfactant. The mixing chamber has a liquid flow channel and a gas inlet channel having particular dimensions including the area of the gas inlet channel that the gas travels through and the liquid flow channel diameter that the liquid flow through and where the gas and the liquid/surfactant meet (see FIG. 5). In one embodiment, the air:liquid ratio of the foam may be adjusted by changing the pressure levels of the gas and the liquid/surfactant as well as the inlet channel diameters.

In one embodiment, the porous material 250 has a specified porosity and wetted surface area that is required to reduce the size of the bubbles in order to achieve a microfoam.

In one embodiment, the foam is captured by the foam transfer receptacle 254. In one embodiment, the foam transfer receptacle may have relief holes around the perimeter of the receptacle to allow for extra gas to escape.

In one embodiment, the system 220 creates foam using a gas to liquid ratio of 4:1. In one embodiment, in order to achieve the desired foam with the a 4:1 gas to liquid ratio, the following parameters are used for the foam making system.

TABLE 1

| Factor | Parameter Setting |
|---|---|
| Liquid/Surfactant | 20% Albumin |
| Gas | Manufactured Air or CO2 or N2 |
| First Gas Regulator | 45 psi |
| Second Gas Regulator | 65 psi |
| Gas Inlet Channel | .008" |
| Liquid Flow Channel | .220" |
| Porosity of Porous Material | 30-35% |

Referring to FIG. 5, in one embodiment, a second gas conduit 278 is coupled with a gas inlet orifice 242 of the mixing chamber 236 for introducing the pressurized gas from the second gas cartridge 264B into the mixing chamber 236. The mixing chamber 236 preferably includes a gas inlet 242 that intersects with the liquid flow channel 245 that extends between the mixing chamber inlet 238 and the mixing chamber outlet 240. As the liquid dispensed from the liquid syringe 222 passes through the liquid flow channel 245, the stream of the second pressurized gas that has entered the gas inlet 242 is mixed with the liquid in the liquid flow channel 245. The mixture of the liquid stream and the second pressurized gas stream is preferably dispensed from the mixing chamber outlet 240, whereupon it is passed downstream to the foaming chamber 244.

Figure 6:
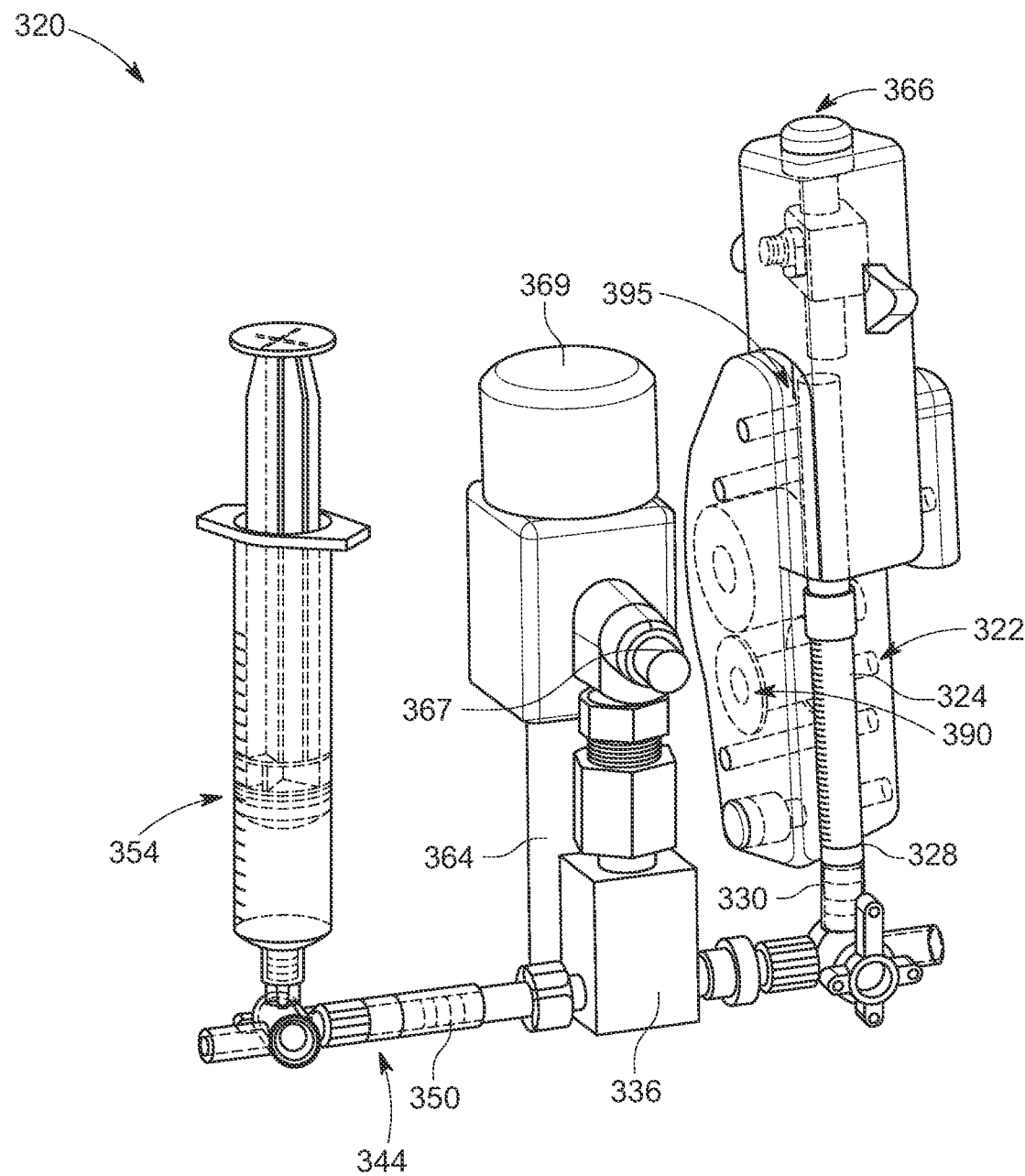
FIG. 6 shows a system for making foam used in medical procedures, in accordance with one embodiment of the present patent application.

In one embodiment, a system for making foam may use a stored energy system or a motor for moving a plunger in a liquid syringe for dispensing a liquid. Referring to FIG. 6, in one embodiment, a system 320 for making foam used in medical procedures preferably includes a liquid syringe 322 that contains a liquid. The system 320 preferably includes a stored energy system including a constant torque spring 390 that is coupled with a plunger 332 for driving the plunger 332 toward the second end 328 of a syringe barrel 324 for dispensing the liquid from a liquid dispensing port 330 at the second end 328 of the syringe barrel 324. In one embodiment, the system 320 preferably includes an actuator button 366 that may be engaged for releasing the constant torque spring 360 for forcing the plunger 332 toward the second end 328 of the syringe barrel 324.

In one embodiment, the system 320 preferably includes a gas cartridge 364 that contains a pressurized gas. The pressurized gas in the gas cartridge 365 is introduced into a mixing chamber 336 when an actuator button 367 is engaged. A regulator 369 preferably regulates the pressure level of the pressurized gas that is introduced into the mixing chamber 336.

In one embodiment, inside the mixing chamber 336, the liquid dispensed from the liquid syringe 336 is mixed with the pressurized gas from the gas cartridge 364. After the liquid and the gas have been mixed together in the mixing chamber 336, the liquid and gas mixture desirably flows downstream to a foaming chamber 344 that contains a porous material 350. The porous material 350 creates a tortuous path for the liquid and gas mixture as it passes through the foaming chamber 344 to form foam that is collected by a foam transfer receptacle 354. In one embodiment, the force generated by the spring 390 and the pressure level of the pressurized gas may be adjusted to control the gas to liquid ratio in the mixing chamber.

In one embodiment, the speed at which the plunger moves in the liquid syringe that contains the liquid/surfactant is driven by the force provided by the constant torque spring 390. In one embodiment, in order to achieve a desired gas to liquid ratio of about 4:1, the following parameters are used for the system 320.

TABLE 1

| Factor | Parameter Setting |
|---|---|
| Constant Force Spring | 20 lbs |
| Gas Regulator | 65 psi |
| Gas Inlet Channel (ID) | .008" |
| Liquid Flow Channel (ID) | .220" |
| Porosity of Porous Material | 30-35% |

Figure 7:
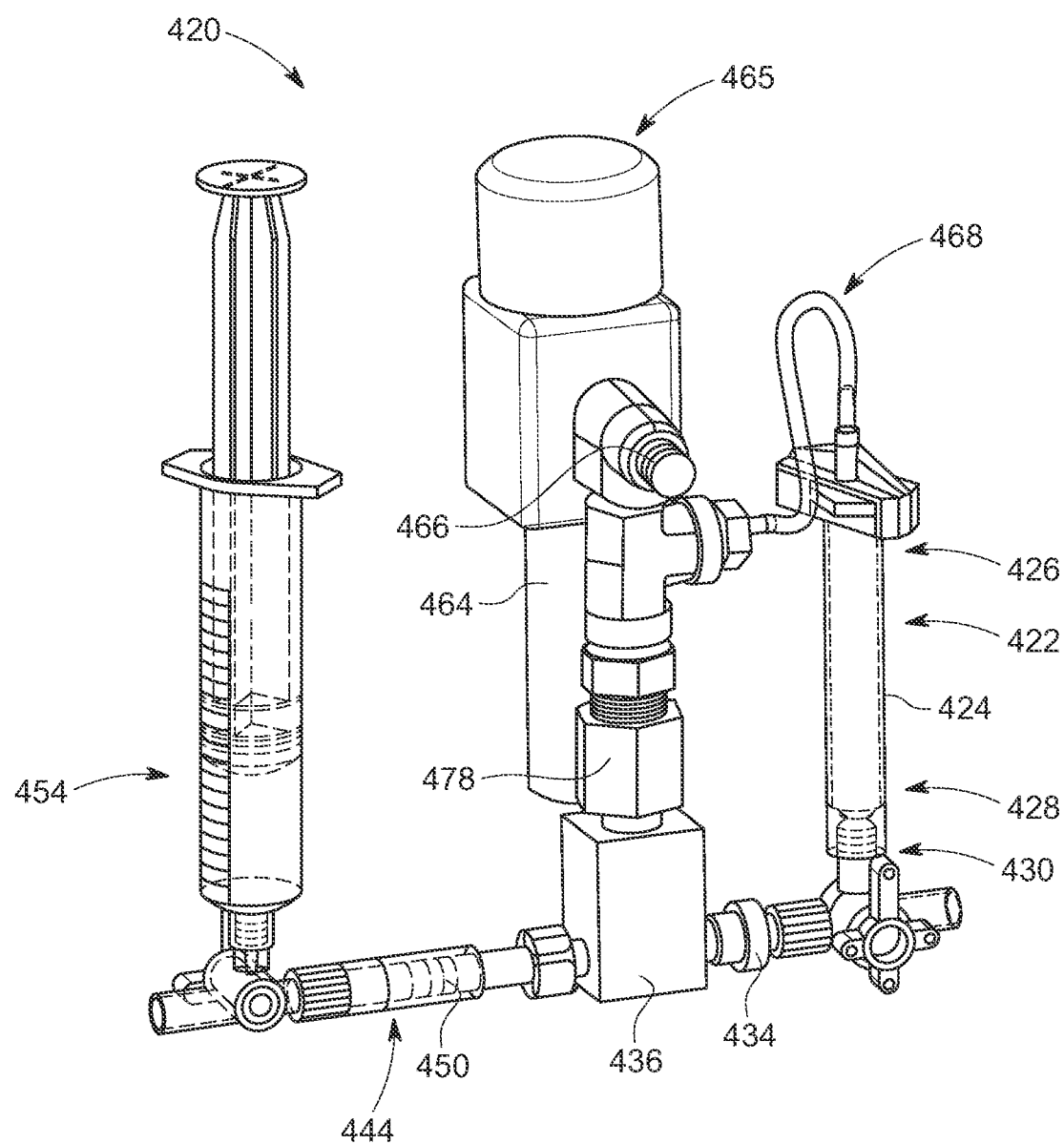
FIG. 7 shows a system for making foam used in medical procedures, in accordance with one embodiment of the present patent application.

In one embodiment, a single source of pressurized gas may be used to actuate a liquid dispenser for dispensing a liquid while also serving as a supply of pressurized gas that is introduced into a stream of the dispensed liquid for making foam. Referring to FIG. 7, in one embodiment, a system 420 for making foam used in medical procedures preferably includes a liquid syringe 422 having a syringe barrel 424 with a first end 426 and a second end 428. A liquid dispensing port 430 is located at the second end 428 of the syringe barrel 424 for dispensing liquid from the syringe barrel 424.

In one embodiment, the system 420 preferably includes a one-way check valve 434 that enables the liquid dispensed from the liquid syringe 422 to flow into a mixing chamber 436, while preventing the dispensed liquid or a gas from reversing direction and backing up into the syringe barrel 424.

In one embodiment, the system 420 desirably includes a gas cartridge 464 that contains a pressurized gas that may be selectively released by engaging an actuator 466. In one embodiment, the system 420 preferably includes a regulator 465 that regulates the pressure level of the pressurized gas introduced into the mixing chamber 436 and/or the first end 426 of the syringe barrel 424.

In one embodiment, the system 420 preferably includes a first gas conduit 468 that passes the pressurized gas from the gas cartridge 464 to the first end 426 of the syringe barrel 424 for forcing the plunger toward the second end 428 of the syringe barrel 424. The system 420 preferably includes a second gas conduit 478 that passes pressurized gas into the mixing chamber 436.

In one embodiment, the liquid dispensed from the liquid syringe 422 and the pressurized gas from the gas cartridge 464 are mixed together within the mixing chamber 436 to form a mixture of liquid and gas that is passed into a foaming chamber 444. The mixture of liquid and gas passes through porous material 450 in the foaming chamber to form foam that is collected by a foam transfer receptacle 454.

Figure 8:
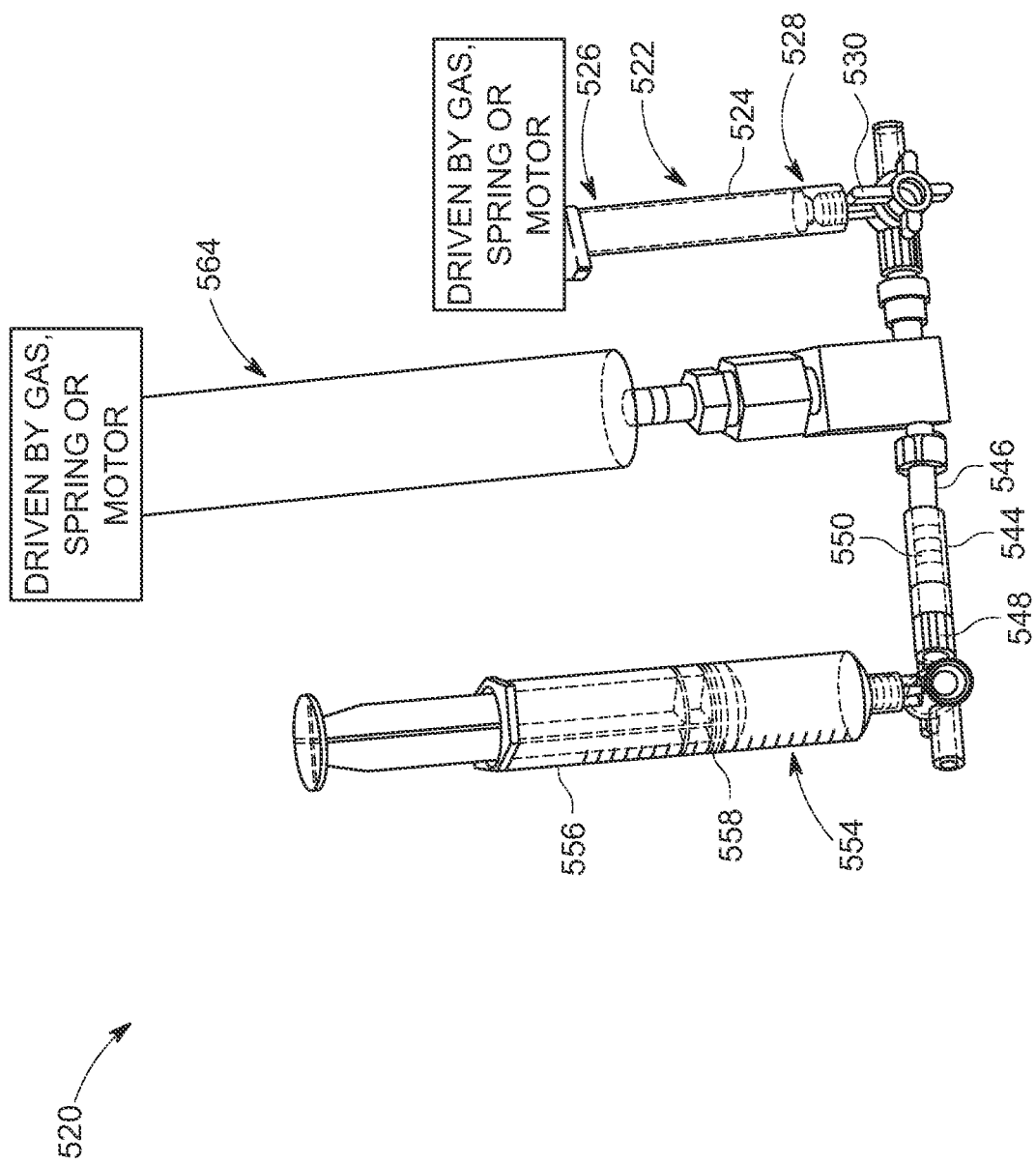
FIG. 8 shows a system for making foam used in medical procedures, in accordance with one embodiment of the present patent application.

In one embodiment, a syringe having a plunger may be used for introducing gas into a stream of dispensed liquid for making foam. Referring to FIG. 8, in one embodiment, a system 520 for making foam used in medical procedures preferably includes a liquid syringe 522 that contains a liquid used for making foam. In one embodiment, the liquid syringe 522 desirably includes a syringe barrel 524 with a first end 526 and a second end 528 having a liquid dispensing port 530. The liquid syringe desirably includes a syringe plunger that may be forced toward the second end of the syringe barrel manually or by pressured gas, a spring, a stored energy system, a gear system, and/or a motor.

In one embodiment, the system 520 preferably includes a gas syringe 564 that contains a supply of gas that is introduced into a mixing chamber 536 for being mixed with the stream of the liquid that is dispensed from the liquid syringe 522. In one embodiment, the gas syringe 562 has a volume of 60 ml or more. The gas syringe 564 preferably has a plunger that is advanced toward the mixing chamber 536 for forcing the gas within the gas syringe into the mixing chamber. The gas syringe 564 may dispense gas having a pressure level that is greater than the pressure level of ambient air or the atmosphere at sea level. The gas syringe desirably includes a syringe plunger that may be forced toward the second end of the syringe barrel manually or by pressured gas, a spring, a stored energy system, a gear system, and/or a motor.

In one embodiment, the liquid disposed within the liquid syringe 522 is dispensed into the mixing chamber 536 at the same time, close in time, or simultaneously as the gas within the gas syringe 564 is introduced into the mixing chamber 536. In one embodiment, the actuators (e.g., plungers) for the respective liquid syringe 522 and gas syringe 564 may be coupled together for simultaneously dispensing the liquid from the liquid syringe as the gas is dispensed from the gas syringe 564.

In one embodiment, after the liquid and the gas have been mixed together in the mixing chamber 536, the liquid and gas mixture travels downstream to a foaming chamber 544 having a foaming chamber inlet 546 and a foaming chamber outlet 548. The foaming chamber 544 preferably contains a porous material that creates a tortuous path for the liquid and gas mixture as the mixture moves from the foaming chamber inlet 546 to the foaming chamber outlet 548. In one embodiment, the system 520 may include a foam transfer receptacle 554 for collecting foam. In one embodiment, the foam transfer receptacle 554 preferably includes a plunger 558 that may be retracted for drawing foam into a foam transfer receptacle barrel 556 of the foam transfer receptacle 554.

While the foregoing is directed to embodiments of the present invention, other and further embodiments of the invention may be devised without departing from the basic scope thereof, which is only limited by the scope of the claims that follow. For example, the present invention contemplates that any of the features shown in any of the embodiments described herein, or incorporated by reference herein, may be incorporated with any of the features shown in any of the other embodiments described herein, or incorporated by reference herein, and still fall within the scope of the present invention.

What is claimed is:

1. A medical device for making foam comprising:
   a syringe including a plunger for dispensing a liquid from a liquid dispensing port;
   a mixing chamber including a mixing chamber inlet in fluid communication with said liquid dispensing port, a mixing chamber outlet spaced from said mixing chamber inlet, a liquid flow channel extending between said mixing chamber inlet and said mixing chamber outlet, and a gas inlet channel that intersects with said liquid flow channel for mixing a gas with said liquid dispensed from said liquid dispensing port;
   a gas cartridge containing said gas;
   a first gas conduit having a first end connected with said gas cartridge and a second end connected with said syringe;

a second gas conduit having a first end connected with said gas cartridge and a second end connected with said gas inlet channel of said mixing chamber;

an actuator coupled with said gas cartridge for selectively releasing said gas from said gas cartridge for flowing into said first and second gas conduits, wherein said released gas in said first gas conduit forces said plunger toward said liquid dispensing port for dispensing said liquid from said liquid dispensing port and into said liquid flow channel while said released gas in said second gas conduit flows into said gas inlet channel of said mixing chamber for mixing with said liquid in said liquid flow channel.

2. The medical device as claimed in claim 1, further comprising a check valve disposed between said liquid dispensing port and said mixing chamber inlet that allows said liquid to flow in only one direction from said liquid dispensing port to said mixing chamber inlet while preventing said gas in said gas inlet channel from passing through said check valve.

3. The medical device as claimed in claim 1, further comprising a foaming chamber including a foaming chamber inlet in fluid communication with said mixing chamber outlet, a foaming chamber outlet, and a porous material disposed within said foaming chamber, wherein said porous material has a tortuous path configured to generate foam as the mixture of said liquid and said gas passes through said porous material.

4. The medical device as claimed in claim 3, wherein said porous material in said foaming chamber has a porosity of about 25-40%.

5. The medical device as claimed in claim 1, further comprising at least one regulator for regulating pressure levels of said gas flowing through said respective first and second gas conduits, wherein said gas in said first gas conduit and said gas in said second gas conduit have different pressure levels.

6. The medical device as claimed in claim 1, wherein said gas in said gas cartridge is pressurized gas having a pressure level of about 45-65 pounds per square inch, and wherein said pressurized gas is selected from the group of gasses consisting of air, carbon dioxide and nitrogen.

7. The medical device as claimed in claim 1, further comprising:
an end cap secured over a first end of said syringe, wherein said end cap forms an air-tight connection with the first end of said syringe;
said end cap having a gas inlet port;
said first gas conduit being connected with said gas inlet port of said end cap.

8. The medical device as claimed in claim 1, wherein said liquid flow channel has an inner diameter that is about 25-30 times larger than an inner diameter of said gas inlet channel.

9. A medical device for making foam comprising:
a syringe including a syringe barrel having a first end, a second end, and a liquid dispensing port located at the second end of said syringe barrel;
a liquid disposed in said syringe barrel;
a plunger disposed within said syringe barrel and being moveable toward said second end of said syringe barrel for dispensing said liquid from said liquid dispensing port;
a mixing chamber comprising
a mixing chamber inlet in fluid communication with said liquid dispensing port,
a mixing chamber outlet spaced from said mixing chamber inlet,
a liquid flow channel extending between said mixing chamber inlet and said mixing chamber outlet, and
a gas inlet channel that intersects with said liquid flow channel;
a check valve disposed between said liquid dispensing port and said mixing chamber inlet that allows said liquid to flow in only one direction from said liquid dispensing port to said mixing chamber inlet;
a gas source including a first gas conduit in fluid communication with said first end of said syringe barrel and a second gas conduit in fluid communication with said gas inlet channel of said mixing chamber;
an actuator coupled with said gas source for simultaneously releasing gas from said gas source into said first and second gas conduits, wherein said released gas in said first gas conduit forces said plunger toward said second end of said syringe barrel for dispensing said liquid from said liquid dispensing port and into said liquid flow channel while said released gas in said second gas conduit flows through said gas inlet channel of said mixing chamber for mixing with said liquid in said liquid flow channel;
a foaming chamber comprising
a foaming chamber inlet in fluid communication with said mixing chamber outlet,
a foaming chamber outlet, and
a porous material disposed within said foaming chamber, wherein the mixture of said liquid and said gas passes through said porous material disposed within said foaming chamber for generating foam that is dispensed from said foaming chamber outlet.

10. The medical device as claimed in claim 9, wherein said liquid disposed in said syringe barrel comprises a surfactant.

11. The medical device as claimed in claim 9, further comprising:
an end cap secured over the first end of said syringe barrel;
said end cap having a gas inlet port;
said first gas conduit being connected with said gas inlet port of said end cap.

12. The medical device as claimed in claim 9, wherein said liquid flow channel has an inner diameter that is larger than an inner diameter of said gas inlet channel.

13. The medical device as claimed in claim 12, wherein the inner diameter of said liquid flow channel is about 25-30 times larger than the inner diameter of said gas inlet channel.

14. The medical device as claimed in claim 9, further comprising:
at least one regulator for controlling a pressure level of said gas in said first gas conduit and said second gas conduit, wherein said gas in said first conduit and said gas in said second gas conduit have different pressure levels.

15. The medical device as claimed in claim 9, wherein said gas in said gas source is pressurized gas having a pressure level of about 45-65 pounds per square inch, and wherein said pressurized gas is selected from the group of gasses consisting of air, carbon dioxide and nitrogen.

16. The medical device as claimed in claim 9, wherein said porous material in said foaming chamber has a porosity of about 25-40%.

17. The medical device as claimed in claim 9, further comprising a foam collection receptacle connected with said foam chamber outlet for collecting foam generated within said foam chamber.

18. A method of making foam used for sealing tissues using the medical device of claim 1 comprising:
    obtaining a container holding a liquid;
    directing a first stream of a gas toward said container for dispensing a stream of said liquid from said container;
    simultaneously with directing said first stream of said gas toward said container, directing a second stream of said gas into said dispensed stream of said liquid for generating a liquid and gas mixture;
    passing said liquid and gas mixture through a porous material for generating foam.

19. The method as claimed in claim 18, further comprising prior to directing said first stream of said gas toward said container, introducing a surfactant into said liquid.

20. The method as claimed in claim 19, further comprising maintaining said first stream of said gas at a pressure level of about 8-45 pounds per square inch.

21. The method as claimed in claim 20, further comprising maintaining said second stream of said gas at a pressure level of about 65 pounds per square inch.

22. The method as claimed in claim 18, further comprising:
    providing a mixing chamber including a mixing chamber inlet, a mixing chamber outlet, a liquid flow channel extending between said mixing chamber inlet and said mixing chamber outlet, and a gas flow channel that intersects with said liquid flow channel;
    directing said dispensed stream of said liquid into said mixing chamber inlet and through said liquid flow channel;
    directing said second stream of said gas into said gas inlet channel of said mixing chamber for introducing said second stream of said gas into said dispensed stream of said liquid.

* * * * *